United States Patent [19]

Cama et al.

[11] 4,321,197

[45] Mar. 23, 1982

[54] 1-CARBA-6-(1-HYDROXYETHYL)-2-CARBO-NYL-PENEM-3-CARBOXYLIC ACID AND PREPARATION THEREOF

[75] Inventors: Lovji D. Cama, Cresskill; Ravindra Guthikonda, Edison; Burton G. Christensen, Scotch Plains, all of N.J.

[73] Assignee: Merck & Co., Inc., Rahway, N.J.

[21] Appl. No.: 219,629

[22] Filed: Dec. 24, 1980

[51] Int. Cl.³ .......................................... C07D 487/04

[52] U.S. Cl. ...................... 260/245.2 T; 260/239 A; 424/274

[58] Field of Search ................................. 260/245.2 T

*Primary Examiner*—Mary C. Lee
*Attorney, Agent, or Firm*—Frank M. Mahon; Hesna J. Pfeiffer

[57] ABSTRACT

Antibiotic 1-carba-6-(1-hydroxyethyl-2-carbonyl-penem-3-carboxylic acid is prepared by total chemical synthesis from 4-iodomethyl-1-(t-butyldimethylsilyl)-2-azetidinone.

2 Claims, No Drawings

1-CARBA-6-(1-HYDROXYETHYL)-2-CARBONYL-PENEM-3-CARBOXYLIC ACID AND PREPARATION THEREOF

The instant invention relates to novel chemical compounds classifiable in the field of organic chemistry as 1-carba-6-(1-hydroxyethyl)-2-penem-3-carboxylic acids and the pharmaceutically acceptable salts thereof. More particularly, the instant invention may be described as residing in the concept of such 1-carba-6-(1-hydroxyethyl)-2-penem-3-carboxylic acids characterized by having a carbonyl group at the 2-position, to a process for preparing such compounds and to antibiotic compositions containing such compounds as an essential active ingredient. In addition, the compounds of formula I, serve as valuable intermediates in the preparation of other active antibiotics.

In its composition aspect therefore, the instant invention may be described as residing in the concept of novel penems having the structure:

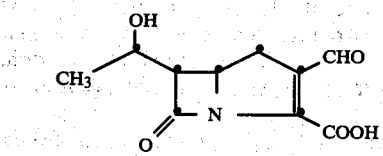

and the pharmaceutically acceptable salts thereof. The instant invention is based on applicants' discovery that the compounds of formula I are active antibiotic agents which may be employed in antibiotic applications either alone or in combination with other antibiotic and antibacterial agents.

The compounds of formula I are prepared according to the process of the instant invention by total synthesis from 4-iodomethyl-1-(t-butyldimethylsilyl)-2-azetidinone (II). The process is summarized by the following reaction diagram:

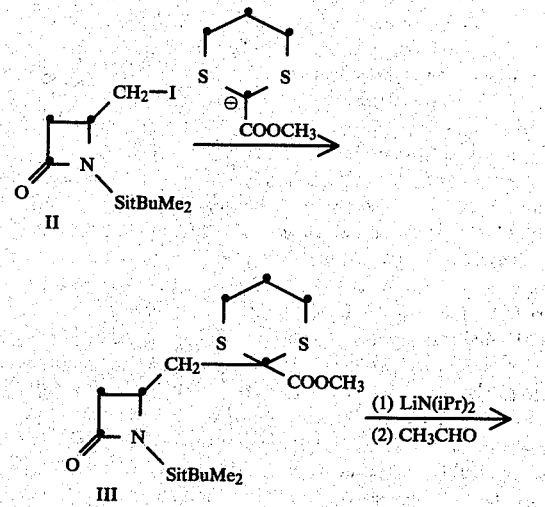

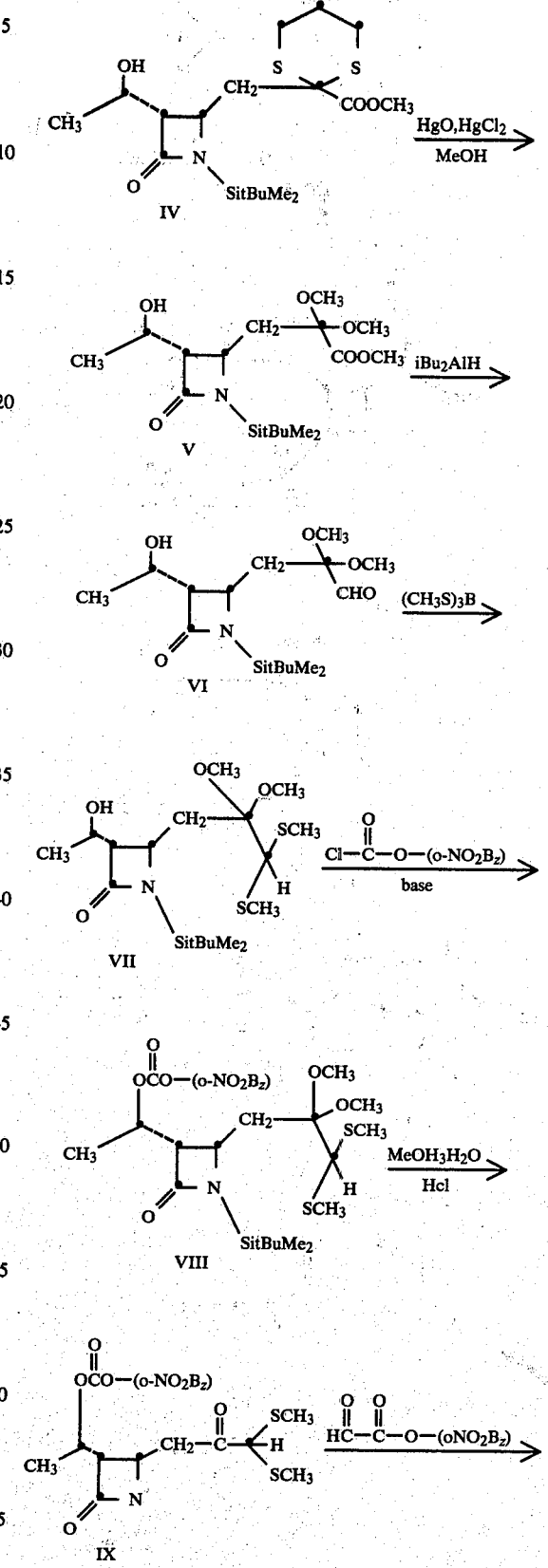

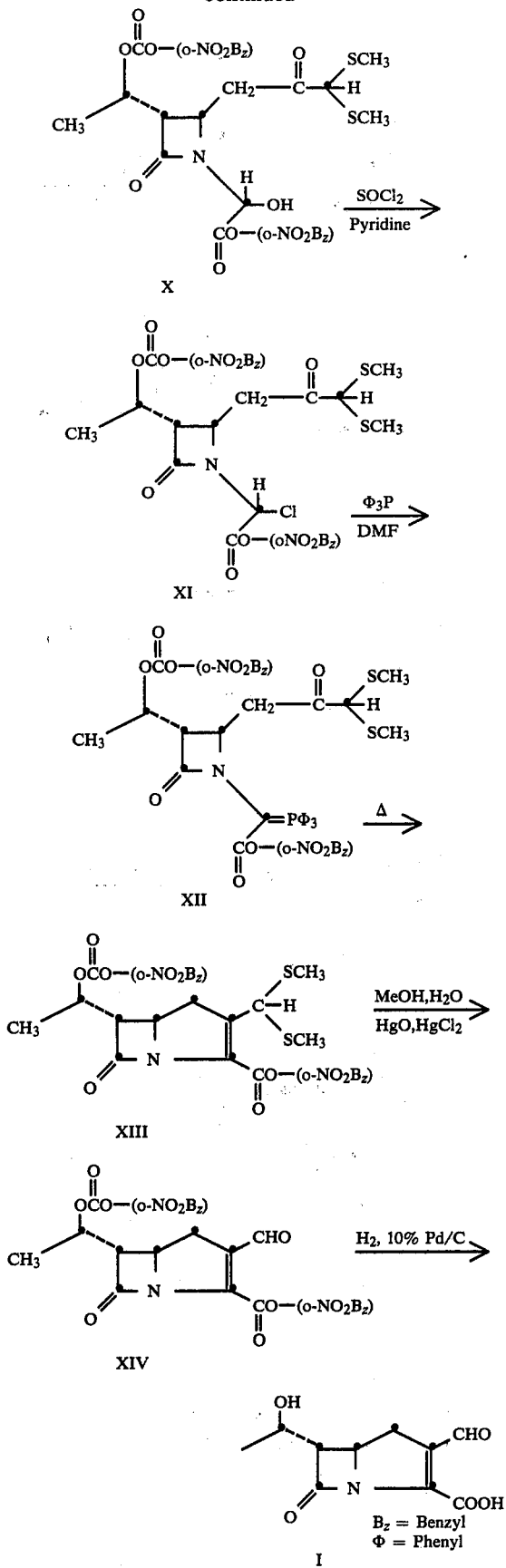

The starting material employed in the process illustrated above, 4-iodomethyl-1-(t-butyldimethylsilyl)-2-azetidinone (II) is a well-known compound readily prepared by techniques already described in the art. Although the t-butyldimethylsilyl as illustrated is the preferred protecting group, other triorganosilyl protecting groups, such as t-butyldiphenylsilyl, triphenylsilyl and isopropyldimethylsilyl, can be employed. Silyl protection typically is achieved by treating 4-iodomethylazetidin-2-one in a solvent, such as dimethylformamide, acetonitrile, hexamethylphosphoramide, tetrahydrofuran and the like, with a silylating agent, such as t-butyldimethylchlorosilane, t-butyldiphenylchlorosilane, triphenylchlorosilane, and the like, at a temperature of from −20° to 25° C. for 0.5 to 24 hours in the presence of a base, such as triethylamine, diisopropylethylamine and imidazole. Such reactions are described in commonly assigned co-pending U.S. application Ser. No. 154,190, filed May 29, 1980, now U.S. Pat. No. 4,290,947.

The transformation, II→III, may be accomplished by treating II in a solvent, such as tetrahydrofuran, dimethylformamide, acetonitrile, and the like, with methyl 1,3-dithiane-2-carboxylate in the presence of a strong base such as n-butyllithium, t-butyllithium, phenyllithium and the like, at a temperature between −100° to −20° C. Usually the reaction is run under nitrogen and is complete in 0.5 to 4 hours. Preferably the dithiane carboxylate is treated with the strong base prior to the addition of II.

The alkylation, III→IV, may be accomplished by treating III in a solvent, such as tetrahydrofuran, dimethoxyethane, diethylether, and the like at a temperature of from −100° to −20° C. with a strong base, such as lithium diisopropylamine, lithium hexamethyldisilazide, and the like, followed by the addition of an equivalent to excess of acetaldehyde. The reaction usually is complete in from 0.5 to 2 hours. The reaction proceeds directly to give a mixture of isomers (trans-R, trans-S and Cis-R) which may be separated by chromatography or by crystallization. The trans-R isomer is preferred.

The transformation, IV→V, is achieved by treating IV in methanol in the presence of a mixture of mercuric oxide and mercuric chloride. The reaction is carried out at reflux and usually is complete in 1 to 4 hours.

The reduction, V→VI, may be accomplished by treating V in a solvent, such as toluene, methylene chloride, tetrahydrofuran, diethylether, and the like, with a reducing agent, such as diisobutylaluminum hydride, sodium bis-(2-methoxyethoxy)alumium hydride and the like, at a temperature of from −100° to −20° C. The reaction, desirably, is run under a nitrogen atmosphere and usually requires 3 to 8 hours for completion.

The addition, VI→VII, is carried out by treating VI in a solvent, such as toluene, hexane, methylene chloride, tetrahydrofuran, and the like, with an equivalent of trimethylthioborane. The reaction is carried out at a temperature between 40° to 70° C., desirably under nitrogen, and usually is complete in 2 to 5 hours.

Establishment of the hydroxyl protecting group, VII→VIII, may be achieved by treating VII in a solvent such as methylene chloride, dimethylformamide, acetonitrile and the like, with an aralkyloxycarbonyl chloride, such as o-nitrobenzyloxycarbonyl chloride and p-nitrobenzyloxycarbonyl chloride, preferrably the o-nitrobenzyloxycarbonyl chloride in the presence of a base, such as pyridine, 4-(N,N-dimethylamino)-pyridine, and the like. The reaction is run at 0° to 50° C., desirably under nitrogen, for 0.5 to 12 hours.

The hydrolysis, VIII→IX, is accomplished by treating VIII with concentrated hydrochloric acid in a loweralkanol, preferably methanol in the presence of water. The reaction proceeds at room temperature and usually is complete in 3 to 6 hours.

The transformation, IX→X, is carried out by reacting IX in a solvent, such as toluene, tetrahydrofuran, dimethylformamide, acetonitrile, and the like, with an aralkylglyoxalate, such as o-nitrobenzylglyoxalate and p-nitrobenzylglyoxalate, the o-nitrobenzylglyoxalate is preferred. The reaction is run at reflux, desirably under a Dean-Stark water separator, for 4 to 8 hours or in the presence of molecular sieves or a dehydrating agent such as $MgSO_4$.

The chlorination, X→XI, may be achieved by treating X in a solvent, such as tetrahydrofuran, and the like, with a chlorinating agent, such as thionyl chloride, in the presence of a base such as pyridine, diisopropylethylamine, triethylamine, and the like. The reaction is run at a temperature between −30° C. to room temperature and usually requires from 0.2 to 1 hour for completion. The chlorinated product, XI, may be treated directly with triphenylphosphine to obtain intermediate, XII. The reaction is carried out at room temperature in a solvent such as dimethylformamide THF, or $CH_2Cl_2$ and usually is complete in 1 to 4 hours.

The cyclization, XII→XIII, is readily achieved by heating XII in a high boiling solvent, such as xylene, at a temperature of from 110° to 150° C. The reaction requires 1 to 3 hours for completion.

The transformation, XIII→XIV, may be carried out by treating XIII in a solvent, such as methanol, ethanol, isopropanol, and the like, at reflux in the presence of mercuric oxide, mercuric chloride and water. The reaction usually is complete in 0.1 to 1 hour.

The final deblocking step, XIV→I, may be carried out by conventional procedures such as hydrogenation. Typically, XIV in a solvent, such as tetrahydrofuran-aqueous ethanol, is treated under a hydrogen pressure of from 20–50 psig in the presence of a catalyst, such as Pd/C, PdOh, and the like. The reaction is run at a temperature of from 25° to 50° C. and usually is complete in from 0.5 to 4 hours. Desirably the reaction mixture is buffered at pH 7 with phosphate buffer and the product is isolated as the alkali metal salt.

The products of this invention, I, form a variety of pharmacologically acceptable salts. The salts of this invention are pharmacologically acceptable non-toxic derivatives which can be used as the active ingredient in suitable unit-dosage pharmaceutical forms. Also they may be combined with other drugs to provide compositions having a broad spectrum of activity.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example, against *Staphylococcus aureus, Escherichia coli, Klebsiella pneumoniae,* Serratia, *Salmonella typhosa,* Pseudomonas and *Bacterium proteus.* The antibacterials of the invention may further be utilized as additives to animal feeding stuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example potato starch or acceptable wetting agents such as sodium lauryl sulphate. The tablets may be coated according to methods well-known in the art. Oral liquid preparations may be in the form of aqueous or oily suspensions, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily ester, propylene glycol, or ethyl alcohol; preservatives, for example, methyl or propyl p-hydroxybenzoates or sorbic acid. Suppositories will contain conventional suppository base, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes, of ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 2 to 600 mg of active ingredient per kg of body weight of the subject in one or more applications per day. A preferred daily dosage for adult humans lies in the range of from about 15 to 150 mg of active ingredient per kg of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10-60%. The composition will generally contain from about 15 mg to about 1500 mg of the active ingredient; however, in general, it is preferable to employ a dosage amount in the range of from about 100 mg to 1000 mg. In parenteral administration the unit dosage is usually the pure compound in a slightly acidified sterile water solution or in the form of a soluble powder intended for solution.

The best mode contemplated by applicants for carrying out their invention is illustrated in the following working examples; no limitation, however, being intended except as set forth in the appended claims.

EXAMPLE 1

Sodium (5R, 6S)-1-Carba-6-(1-hydroxyethyl)-2-carbonyl-2-penem-3-carboxylate (I)

Step A: (4R)-1-(t-Butyldimethylsilyl)-4-[2,2-(trimethylenedithia)-2-(methoxycarbonyl)ethyl]-azetidin-2-one (III)

Dissolve 192 g (1 mole) of ethyl 1,3-dithiane-2-carboxylate in 1 L of methanol and add 5 ml of concentrated hydrochloric acid. Stir at room temperature for 18 hours. Neutralize the mixture with 1 N sodium hydroxide and remove the methanol under reduced pressure. Take up the residue in 1 L of ether, wash with water, dry over magnesium sulfate and evaporate. Distil the residue under reduced pressure to obtain methyl-1,3-dithiane-2-carboxylate.

Dissolve 5.3 g (0.03 mole) of methyl-1,3-dithiane-2-carboxylate in 50 ml of anhydrous tetrahydrofuran and cool under nitrogen to −78° C. Add a solution containing 0.033 moles of n-butyl lithium in hexane dropwise and stir the mixture at 78° C. for 0.5 hours. Add a solution of 9.7 g (0.03 mole) of 4-iodomethyl-1-(t-butyldimethylsilyl)-2-azetidinone, II, in 20 ml of tetrahydrofuran. Stir at −78° C. for 1 hour. Add a saturated solution of ammonium chloride and allow the mixture to warm to room temperature. Separate the organic phase and extract the aqueous phase twice with ether. Wash the combined organic phase with brine, dry over magnesium sulfate and evaporate. Chromatograph over silica gel to give the title product.

Step B: (3S, 4R)-1-(t-Butyldimethylsilyl)-3-(1R)-hydroxyethyl-4-[2,2-(trimethylenedithia)-2-(methoxycarbonyl)ethyl]-azetidin-2-one (IV)

Add by syringe 14.8 ml (0.037 mole) of a 2.5 N solution of n-butyl lithium to a solution of 3.7 g (0.037 mole) of diisopropylamine in 180 ml of anhydrous tetrahydrofuran at −78° C. Stir the mixture for 15 minutes at −78° C. Add a solution 12 g (0.032 mole) of (4R)-1-(t-butyldimethylsilyl)-4-[2,2-(trimethylenedithia)-2-(methoxycarbonyl)-ethyl]-azetidin-2-one in 35 ml of tetrahydrofuran. Stir at −78° C. for 10 minutes and add 4.82 g (0.105 mole) of acetaldehyde. Continue stirring at −78° C. for 5 minutes. Quench with saturated aqueous ammonium chloride solution and allow the mixture to warm to room temperature. Pour the reaction mixture into 250 ml of ether, wash with water and brine, dry over magnesium sulfate and evaporate to a residue. Chromatograph over silica gel to obtain the title product.

Step C: (3S, 4R)-1-(t-Butyldimethylsilyl)-3-(1R)-hydroxyethyl-4-[2,2-(dimethoxy)-2-(methoxycarbonyl)-ethyl]-azetidin-2-one (V)

Dissolve 4.19 g (0.01 mole) of (3S, 4R-1-(t-butyldimethylsilyl)-3-(1R)-hydroxyethyl-4-[2,2-(trimethylenedithia)-2-(methoxycarbonyl)-ethyl]-azetidin-2-one in 50 ml of methanol. Add 1.5 equivalents of mercuric oxide and 2.2 equivalents of mercuric chloride and reflux the mixture for 2 hours. Filter and wash the residue with methanol. Evaporate the filtrate and washings to 10 ml, dilute with 60 ml of ethyl acetate, wash with saturated ammonium chloride solution, dry over magnesium sulfate and evaporate to a residue. Chromatograph over silica gel to obtain the title product.

Step D: (3S, 4R)-1-(t-Butyldimethylsilyl)-3-(1R)-hydroxyethyl-4-[2,2-(dimethyl)-2-(carbonyl)-ethyl]-azetidin-2-one (VI)

Dissolve 3.7 g (0.01 mole) of (3S, 4R)-1-(t-butyldimethylsilyl)-3-(1R-hydroxyethyl-4-[2,2-(dimethoxy)-2-(methoxycarbonyl)-ethyl]-azetidin-2-one in 30 ml of toluene and cool to −78° C. under nitrogen. Add 20 ml of a 1 M solution of diisobutylaluminum hydride in hexane over a 5 minute period. Stir at −78° C. for 6 hours. Add 20 ml of saturated ammonium chloride solution and allow the reaction mixture to warm to room temperature. Separate the organic phase, dry over magnesium sulfate and evaporate to a residue. Chromatograph over silica gel to obtain the title product.

Step E: (3S, 4R)-1-(t-Butyldimethylsilyl)-3-(1R)-hydroxyethyl-4-[2,2-(dimethoxy)-3,3-(dimethylthio)-propyl]-azetidin-2-one (VII)

Dissolve 3.45 g (0.01 mole) of (3S,4R)-1-(t-butyldimethylsilyl)-3-(1-R-hydroxyethyl)-4-[2,2-(dimethoxy)-2-(carbonyl)-ethyl]-azetidin-2-one in 30 ml of toluene under nitrogen and add 1.52 g (0.01 mole) of trimethylthioborane. Heat the mixture at 50° C. for 3 hours. Cool to room temperature and quench with saturated ammonium chloride solution. Separate the organic phase, dry over magnesium sulfate and evaporate to a residue. Chromatograph the residue over silica gel to obtain the title product.

Step F: (3s,4R)-1-(t-Butyldimethylsilyl)-3-(1R)-o-nitrobenzyloxycarbonyloxyethyl-4-[2,2-(dimethoxy)-3,3-(dimethylthio)propyl]-azetidin-2-one (VIII)

Dissolve 4.2 g (0.01 mole) of (3S, 4R)-1-(t-butyldimethylsilyl)-3-(1R)-hydroxyethyl-4-[2,2-(dimethoxy)-3,3-(dimethylthio)-propyl]-azetidin-2-one in 100 ml of methylene chloride and cool to 0° C. under nitrogen. Add 4.29 g (0.02 mole) of O-nitrobenzyloxycarbonyl chloride and 2.4 g (0.02 mole) of 4-(N,N-dimethylamino)-pyridine. Stir at 0° C. for 0.5 hours and then for 3 hours at room temperature. Wash the reaction mixture with water, dry over magnesium sulfate and evaporate to a residue. Chromatograph over silica gel to obtain the title product.

Step G: (3S, 4R)-3-(1R)-o-Nitrobenzyloxycarbonyloxyethyl-4-[2-oxo-3,3-(dimethylthio)propyl]-azetidin-2-one (IX)

Dissolve 5.0 g (0.01 mole) of (3S, 4R)-1-(t-butyldimethylsilyl)-3-[(1R)-o-nitrobenzyloxy-carbonyloxyethyl-4-[2,2-(dimethoxy)-3,3-(dimethylthio)-propyl]]-azetidin-2-one in 100 ml of methanol and add 1.66 ml of concentrated hydrochloric acid. Stir at room temperature for 2 hours. Neutralize by adding excess 5% sodium bicarbonate solution. Evaporate to a residue under reduced pressure. Extract the residue with methylene chloride, dry over magnesium sulfate and evaporate to a residue. Chromatograph the residue over silica gel to obtain the final product.

Step H: (3S, 4R)-1-(o-Nitrobenzyloxycarbonylhydroxy)methyl-3-(1R)-o-nitrobenzyloxycarbonyloxyethyl-4-[2-oxo-3,3-(dimethylthio)-propyl]-azetidin-2-one (X)

Dissolve 2.09 g (0.01 mole) of o-nitrobenzylglyoxalate in 40 ml of toluene and add 1.89 g (0.005 mole) of (3S, 4R)-3-(1R)-o-nitrobenzyloxycarbonyloxyethyl-4-[2-oxo-3,3-(dimethylthio)propyl]-azetidin-2-one. Reflux under a Dean-Stark water separator containing CaH₂ for 6 hours. Cool the reaction mixture to room temperature and remove the toluene under reduced pressure. Chromatograph the residue over silica gel to obtain the title product.

Step I: (3S, 4R)-1-(o-nitrobenzyloxycarbonylchloro)-methyl-3-(1R)-orthonitrobenzoyloxycarbonyloxyethyl-4-[2-oxo-3,3-(dimethylthio)propyl]-azetidin-2-one (XI)

Treat 2.9 g (0.005 mole) of (3S, 4R)-1-(o-nitrobenzyloxycarbonylhydroxy)-methyl-3-(1R)-o-nitrobenzyloxycarbonyloxyethyl-4-[2-oxo-3,3-(dimethylthio)-propyl]-azetidin-2-one with 1.2 equimolar amounts of pyridine and SOCl₂ in 30 ml of tetrahydrofuran at −20° C. Remove the cooling bath after 10 minutes and continue stirring for a further 20 minutes. Filter and wash the residue with anhydrous ether. Evaporate the filtrate and washings to obtain the title product which is employed without purification in the next step.

Step J: (3S, 4R)-1-(o-Nitrobenzyloxycarbonyltriphenylphosphoranylmethyl)-3-(1R)-o-nitrobenzyloxycarbonyloxyethyl-4-[2-oxo-3,3-(dimethylthio)-propyl]-azetidin-2-one (XII)

Dissolve the (3S, 4R)-1-(o-nitrobenzyloxycarbonylchloromethyl)-3-(1R)-(o-nitrobenzyloxycarbonyloxyethyl)-4-[2-oxo-3,3-(dimethylthiopropyl]-azetidin-2-one in 20 ml of dimethylformamide and add 0.005 mole of triphenylphosphine. Stir at room temperature for 1.5 hours. Remove the dimethylformamide under reduced pressure. Take up the residue in methylene chloride, wash with 5% sodium bicarbonate solution, dry over magnesium sulfate and evaporate to a residue. Chromatograph the residue over silica gel to obtain the title product.

Step K: o-Nitrobenzyl (5R, 6S)-1-Carba-6-(1R)-o-nitrobenzyloxycarbonyloxyethyl)-2-(dimethylthio)-methyl-2-penem-3-carboxylate (XIII)

Dissolve 2.1 g of (3S, 4R)-1-(o-nitrobenzyloxycarbonyltriphenylphosphoranylmethyl)-3-(1R)-o-nitrobenzyloxycarbonyloxyethyl)-4-[2-oxo-3,3-(dimethylthio)-propyl]-azetidin-2-one in 30 ml of xylene and heat to 130° C. for 1.5 hours. Cool the reaction mixture to room temperature and remove the xylene under reduced pressure. Chromatograph the residue over silica gel to obtain the title product.

Step L: o-Nitrobenzyl (5R, 6S)-1-Carba-6-(1-o-nitrobenzyloxycarbonyloxyethyl)-2-carbonyl-2-penem-3-carboxylate (XIV)

Dissolve 0.62 g (0.001 mole) of o-nitrobenzyl (5R, 6S)-1-carba-6-(1R)-o-nitrobenzyloxycarbonyloxyethyl-2-(dimethylthio)-methyl-2-penem-3-carboxylate in 20 ml of ethanol, 2 ml of water, 0.0015 mole of mercuric oxide and 0.0022 mole of mercuric chloride and reflux for 15 minutes. Filter the reaction mixture and wash the residue with ethanol. Evaporate the filtrate and washings to 5 ml. Dilute with ethyl acetate, wash with water, dry over magnesium sulfate and evaporate to a residue. Chromatograph over silica gel to obtain the title product.

Step M: Sodium (5R, 6S)-1-Carba-6-(1-hydroxyethyl)-2-carbonyl-2-penem-3-carboxylate (I)

Dissolve 5 mg of o-nitrobenzyl (5R, 6S)-1-carba-6-(1-o-nitrobenzyloxycarbonyloxyethyl)-2-carbonyl-2-penem-3-carboxylate in 10 ml of tetrahydrofuran. Add 6 ml of water, 2 ml of ethanol and 1 ml of pH 7 phosphate buffer. Add 5 mg of 10% Pd/C catalyst. Hydrogenate at 40 psig hydrogen pressure for 15 minutes. Separate the catalyst by filtration and wash with water. Extract the filtrate and washings three times with ether. Freeze-dry the aqueous phase to obtain the title product.

The subject matter which applicants regard as their invention is particularly pointed out and distinctly claimed as follows:

1. A compound of the formula:

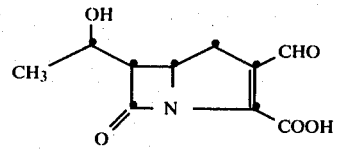

and the pharmaceutically acceptable salts thereof.

2. A process for preparing a compound of claim 1 which comprises:
    (a) reacting 4-iodomethyl-1-(t-butyldimethylsilyl)-2-azetidinone with methyl 1,3-dithiane-2-carboxylate to obtain 1-(t-butyldimethylsilyl)-4-[2,2-(trimethylenedithia)-2-(methoxycarbonyl)-ethyl]-azetidin-2-one;
    (b) treating the azetidin-2-one of step (a) in the presence of a strong base with acetaldehyde to obtain 1-(t-butyldimethylsilyl)-3-(1-hydroxyethyl)-4-[2,2-(trimethylenedithia)-2-(methoxycarbonyl)-ethyl]-azetidin-2-one;
    (c) treating the azetidin-2-one of step (b) with a mixture of mercuric oxide and mercuric chloride in methanol to obtain 1-(t-butyldimethylsilyl)-3-(1-hydroxyethyl)-4-[2,2-(dimethoxy-2-methoxycarbonyl)-ethyl]-azetidin-2-one;
    (d) reducing the azetidin-2-one of step (c) to obtain 1-(t-butyldimethylsilyl)-3-(1-hydroxyethyl)-4-[2,2-(dimethoxy)-2-(carbonyl)-ethyl]-azetidin-2-one;
    (e) treating the azetidin-2-one of step (d) with trimethylthio borane to obtain 1-(t-butyldimethylsilyl)-3-(1-hydroxyethyl)-4-[2,2-(dimethoxy-3,3-(dimethylthio)-propyl]-azetidin-2-one;
    (f) blocking the hydroxy group of the azetidin-2-one of step (e) with o-nitrobenzyloxycarbonyl chloride in the presence of a base to obtain 1-(t-butyldimethylsilyl)-3-[1-(o-nitrobenzyloxycarbonyloxy)]-4-[2,2-(dimethoxy)-3,3-(dimethylthio)-propyl]-azetidin-2-one;
    (g) hydrolizing the azetidin-2-one of step (f) with alcoholic hydrochloric acid to obtain 3-(1-o- nitrobenzyloxycarbonyloxyethyl)-4-[2-oxo-3,3-(dimethylthio)-propyl]-azetidin-2-one.
(h) treating the azetidin-2-one of step (g) o-nitrobenzylglyoxalate to obtain 1-(o-nitrobenzyloxycarbonylhydroxy)-methyl-3-(o-nitrobenzyloxycarbonyloxyethyl)-4-[2-oxo-3,3-(dimethylthio)-propyl]-azetidin-2-one;
(i) chlorinating the azetinin-2-one of step (h) to obtain 1-(o-nitrobenzyloxycarbonylchloro)-methyl-3-(1-o-nitrobenzyloxycarbonyloxyethyl)-4-[2-oxo-3,3-(dimethylthio)-propyl]-azetidin-2-one;
(j) treating the chlorinated product of step (i) with triphenylphosphene to obtain 1-(o-nitrobenzyloxycarbonyltriphenylphosphoranylmethyl)-3-(1-o-nitrobenzyloxycarbonyloxyethyl)-4-[2-oxo-3,3-(dimethylthio)-propyl]-azetidin-2-one;
(i) cyclizing the azetidin-2-one of step (g) by heating at 110°–150° C. to obtain o-nitrobenzyl-1-carba-6-(1-o-nitrobenzyloxycarbonyloxyethyl)-2-(dimethylthio)-methyl-2-penem-3-carboxylate;
(1) treating the penem of step (k) at reflux in the presence of mercuric oxide, mercuric chloride and water to obtain o-nitrobenzyl-1-carba-6-(1-o-nitrobenzyloxycarbonylethyl)-2-carbonyl-2-penem-3-carboxylate; and
(m) deblocking the penem of step (1) to obtain the desired product of claim 1.

* * * * *